United States Patent [19]

Nakahara et al.

[11] Patent Number: 4,974,261
[45] Date of Patent: Nov. 27, 1990

[54] OPTICAL SURFACE INSPECTION METHOD

[75] Inventors: Tomoharu Nakahara, Nishinomiya; Shinji Hatazawa, Shijonawate; Shozo Nomura, Hirakata; Toshinori Inoue, Nara; Mitsuru Shirasawa; Satoshi Yamatake, both of Osaka, all of Japan

[73] Assignee: Matsushita Electric Works, Ltd., Kadoma, Japan

[21] Appl. No.: 433,823

[22] Filed: Nov. 9, 1989

[30] Foreign Application Priority Data

Nov. 15, 1988 [JP] Japan .................................. 63-288167
Mar. 15, 1989 [JP] Japan .................................. 01-63120

[51] Int. Cl.⁵ .............................................. G06K 9/48
[52] U.S. Cl. ...................................... 382/22; 356/237; 358/106; 382/8
[58] Field of Search ....................... 382/22, 8; 358/106; 356/237, 238

[56] References Cited

U.S. PATENT DOCUMENTS 4,207,593  6/1980  Deutsch ........................... 358/106
4,512,663  4/1985  Bailey .............................. 356/237
4,817,184  3/1989  Thomason ....................... 382/22
4,863,275  9/1989  Cormack ......................... 358/106

Primary Examiner—Leo H. Boudreau
Assistant Examiner—Steven P. Fallon
Attorney, Agent, or Firm—Armstrong, Nikaido, Marmelstein, Kubovcik & Murray

[57] ABSTRACT

An optical surface inspection method inspects a surface defect such as a crack, stain, and irregularity of an article, based upon an original grey value image of two dimensional configuration of the article and also upon an edge image representing a border line of the article surface. An area confined by the border line in the edge picture image is scanned for an edge which may be indicative of the defect. The pixel detected to have the edge is marked as a flag point. A plurality of pixels in the vicinity of the flag point are selected to be arranged in a direction generally perpendicular to the edge direction so that the selected pixels are evaluated in terms of their grey values whether there is a critical change between the selected pixels. When the critical change is acknowledged, the scanned edge is judged to be a clear transition between two contrasted regions and thus indicative of a defect.

11 Claims, 17 Drawing Sheets

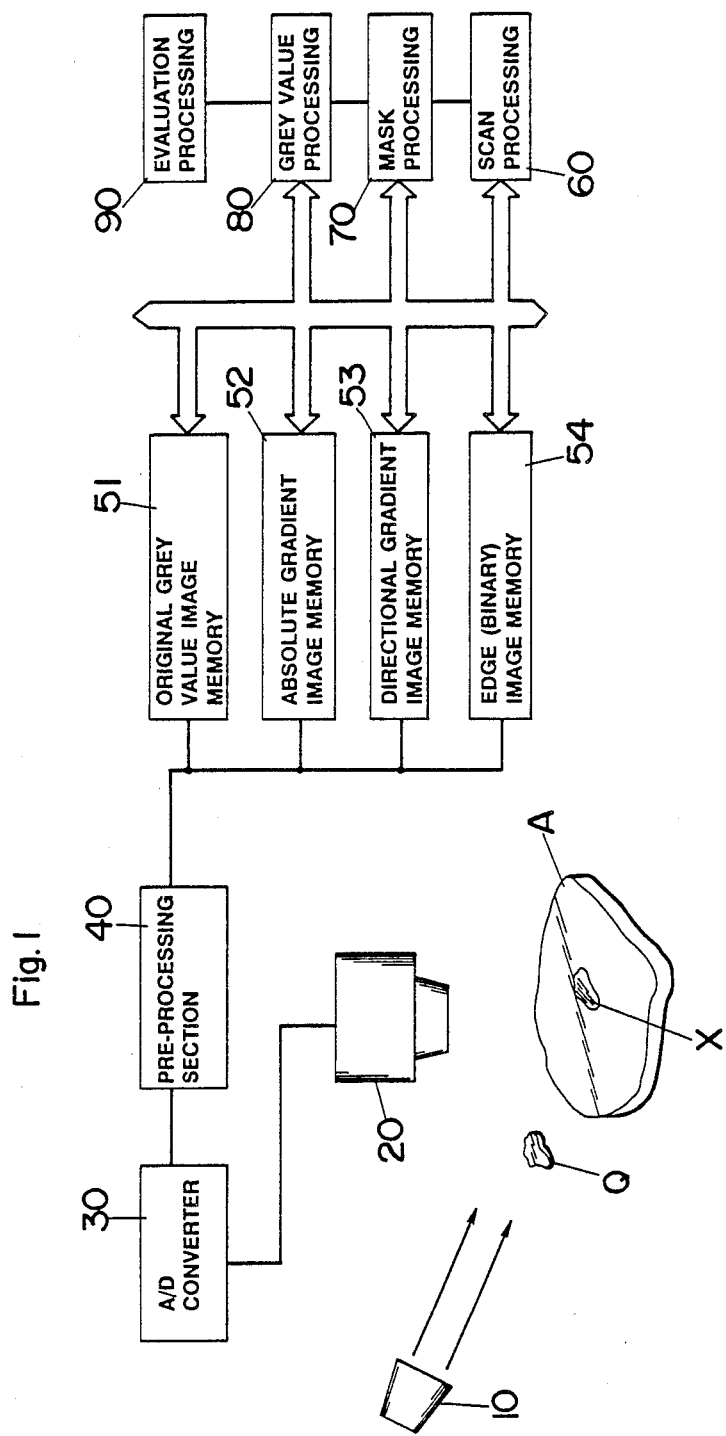
Fig. I

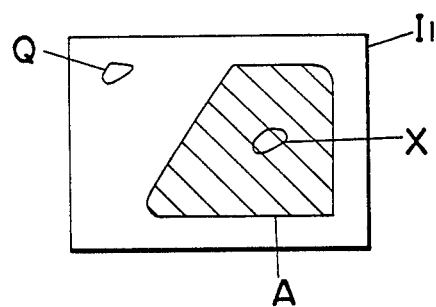
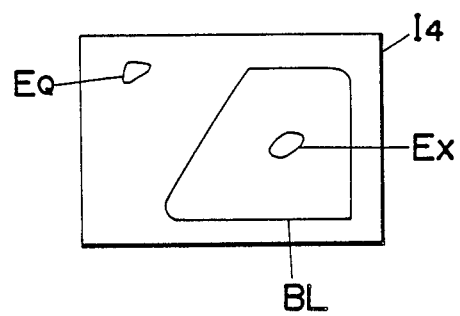
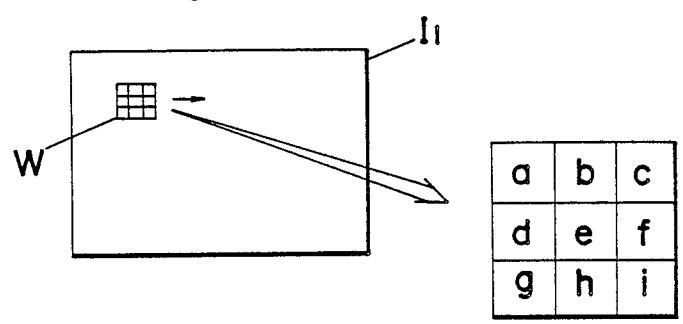
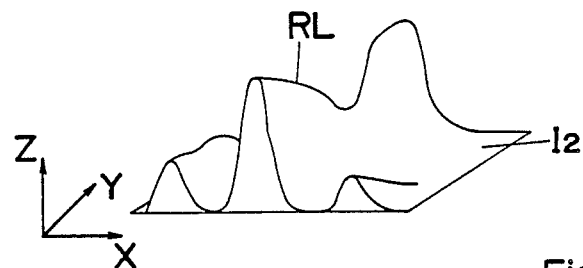
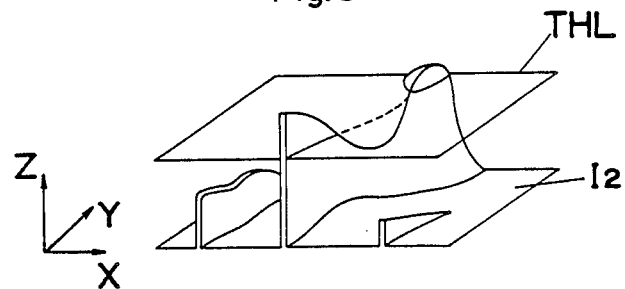

OPTICAL SURFACE INSPECTION METHOD

BACKGROUND OF THE INVENTION

1. Field of the Invention

The present invention is directed to an optical surface inspection method, more particularly to a method for optical inspection of a defect such as a crack, stain, and irregularity of an article.

2. Description of the Prior Art

There has been a growing demand for optical surface inspection which employs digital image processing for rapid and reliable inspection of a surface defect of an article such as a minute electronic component. In a known inspection system utilizing the digital image processing as disclosed, for example, in the Japanese Early publication No. 62-88946, an image transducer such as a TV camera takes a grey value image of a substantially two-dimensional configuration of an article to be inspected. The grey value image is composed of a number of picture elements or pixels having individual grey values. The grey value of each pixels in the image is compared with a suitable threshold value to provide a binary image which is then analyzed for evaluation of a defect. That is, in this prior image evaluation, a transition between two binary values is judged to be indicative of the defect. However, a serious problem has been encountered in such defect evaluation technique. For instance, it fails to discriminate a defect of which pixel has the grey value on the same side of the threshold value as the grey value of the adjacent pixels of a normal non-defective area. In other words, the threshold value is not effective for recognize such a defect that shows a rather vague border edge line or transition between a defective area and a non-defective area.

SUMMARY OF THE INVENTION

The above problem is eliminated in the present invention which provides an improved method for optical surface inspection. In the method of the present invention, an article surface to be inspected is processed to provide an original grey value image and an edge picture image. The original grey value image is a two-dimensional image composed of a number of pixels having individual grey values representing the state of lightness of the article surface. The edge picture image is a binary image representing a border line of the article surface and an edge which may be indicative of a defect such as a crack, stain, indentation or like surface irregularities. The edge picture image is scanned for detecting the edge within the boarder line of the article surface. When the edge is detected in the scanning operation, a flag point is designated at the pixel where a scan line transverses with the edge. Then, a plurality of the pixels in the vicinity of the flag point are selected which are arranged in the direction substantially perpendicular to the edge direction on the respective sides of the flag point. The selected pixels are evaluated, in terms of their grey values of the corresponding pixels in the original grey value image, whether there is a critical change between the pixels on the opposite sides of the flag point. In this manner, a plurality of the pixels around the flag point can be considered to enhance the contrast between the regions on the opposite sides of the edge, whereby assuring improved and precise defect evaluation. Consequently, it is possible with the method of the present invention to reliably detect even a vague defect which only shows a poor contrast in relation to the adjacent normal region and is therefore difficult to be detected by the prior surface inspection.

Accordingly, it is a primary object of the present invention to provide an improved optical surface inspection method which is capable of enhancing the edge of the defect so as to detect even a defect exhibiting less contrast against the normal region of the article surface and therefore improving defect inspection accuracy.

In one version of the present invention, a search track is elected within the confines of the border line of the article surface based upon the edge or binary image for local detection of the edge. The search track is traced to define the flag point at which the search track transverses the edge. Then, the pixels are selected which are arranged along the search track on the opposite sides of the flag point so as to define a mask of the selected pixels. The mask includes more than one symmetrical pair of the pixels which are disposed symmetrically on opposite sides of the core pixel such that the mask extends over several pixels across the edge. The grey values of the two pixels in each symmetrical pair are taken to determine an individual difference therebetween. The individual grey value differences thus determined for all the symmetrical pairs are added to provide a sum which is compared with a predetermined reference value for more exact and consistent evaluation whether or not the detected edge is truly indicative of a surface defect.

It is therefore another object of the present invention to provide an improved optical surface inspection method which provides a mask of several pixels arranged symmetrically across the edge to obtain the sum of the individual grey value differences between the pixels in the symmetrical pair and examine that sum in comparison with a suitable reference value for assuring reliable and consistent defect evaluation.

In another version of the present invention, an inspection zone is elected in the edge image to be located within the confines of the border line of the article surface. The inspection zone is scanned for an edge so as to determine an initial flag point at which a scan line firstly transverses the edge. Starting from thus determined initial flag point, the edge is continuously traced to determine additional flag points which define with the initial flag point a series of flag points arranged along the edge direction. For each of the flag points, a plurality of the pixels are selected which are arranged in a direction generally perpendicular to the edge direction and define an extended mask in which more than one pair of the selected pixels are arranged symmetrically on the opposite sides of the core pixel. The mask are analyzed to determine, in accordance with the corresponding pixels in the original grey value image, whether there is a critical change in the grey values between the pixels in the symmetrical pair or to determine whether one of the pixels in the symmetrical pair has the grey value critically deviated from a predetermined threshold value. Such critical change in the grey value or deviation of the grey value is determined successively for the individual masks provided along the edge direction until there is judged a true presence of the defect. With this technique of analyzing the successive points of the edge in view of the grey values of several pixels arranged across each of that points while following the edge direction, a more precise and consistent defect evaluation can be achieved, which is therefore a further object of the present invention.

The present invention discloses a further advantageous method of precisely detecting a surface irregularity such as a dent or protrusion on the article surface. In this method, a light is directed to the article surface with the illuminating direction being inclined with respect to the article surface and inclined also to a light receiving direction of a TV camera producing the grey value image of the illuminated article surface. In such illuminating circumstance, it may be difficult to obtain a clear image or well contrasted image for the surface irregularity defect, for example, a minute projection or depression, or even large one having an inclined periphery. For eliminating the difficulty due to the inclined illumination and reliably inspecting such surface irregularity, an effective analysis is made to a grey value distribution taken along an inspection line which extends along the illuminating direction. The inspection line is selected to pass a center point on which the successive flag points arranged along the edge direction are centered. Based upon thus obtained grey value distribution, a maximum grey value and a minimum grey value are respectively extracted from a set of continuously appearing grey values exceeding a suitable white threshold value and from an adjacent set of continuously appearing grey values falling below a suitable black threshold value. A difference is calculated between the maximum and minimum grey values and is then compared with a reference value such that the edge can be evaluated in well consideration of a particular grey value variation appearing along the illuminating direction due to the inclined illumination, whereby compensating for the grey value variation to assure reliable inspection of the surface irregularity defect.

It is therefore a still further object of the present invention to provide an improved optical surface inspection method which is capable of reliably detecting a surface irregularity such as a dent or protrusion on the article surface, even with the use of the inclined illumination.

These and still other objects and advantages of the present invention will become more apparent from the following description of the embodiments of the present invention when taken in conjunction with the attached drawings.

BRIEF DESCRIPTION OF THE DRAWINGS

FIG. 1 is a block diagram of an optical surface inspection system in accordance with the present invention;

FIG. 2 is a schematic view of an original grey value image of an area including an article surface to be inspected;

FIG. 3 is a schematic view of an edge image obtained from the above grey value image;

FIG. 4 is a schematic view of an array of pixels arranged in a square illustrating one particular pixels and eight neighbors thereof;

FIG. 5 is a schematic view of an absolute gradient image obtained from the above grey value image;

FIG. 6 is a schematic view illustrating the image of FIG. 5 sliced by a reference threshold level for removing a noise factor prior to effecting a thinning process to obtain the edge image;

DETAILED DESCRIPTION OF THE PREFERRED EMBODIMENTS

Figure 7:
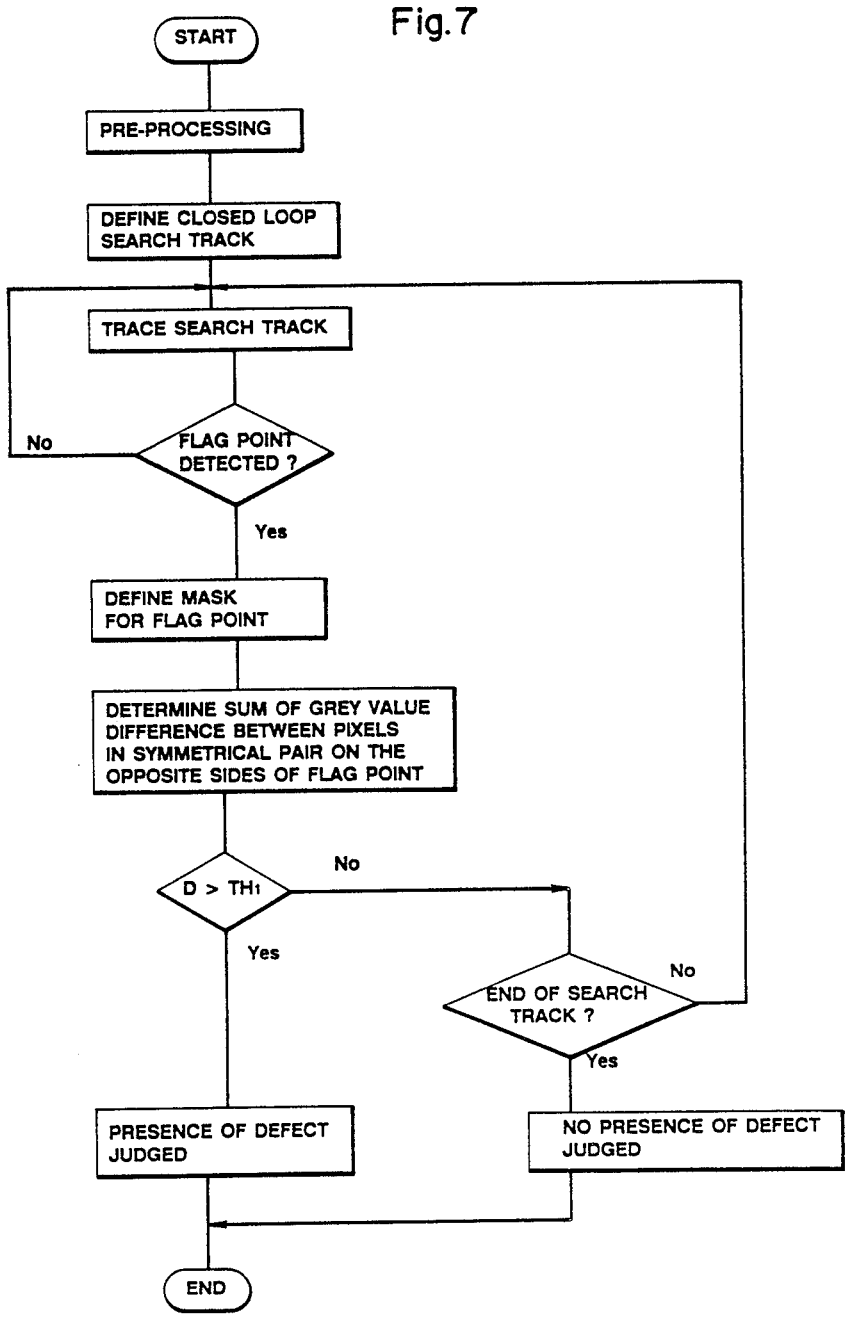
FIG. 7 is a flow chart of the optical surface inspection system in accordance with a first embodiment of the present invention.

An optical surface inspection method of the present invention is designed for testing a circuit board, although not limited thereto, to detect a surface defect in or on conductors and electronic components forming the circuit board. Such defect may be a stain, dent, pinhole, crack, protrusion, and the like surface irregularity which may sometimes make the circuit board unacceptable. For rapid and consistent inspection of the surface defect, the present method is preferred to inspect a particular region of an intended article surface, which region is locally selected in accordance with a known pattern of the article surface.

In preferred embodiments of the present invention, the defect is analyzed based upon an original picture image (grey value image) of the article surface and an edge image (binary image) which is obtained from the grey value image and includes an edge indicative of the defect. Further, the grey value image is processed to provide two other images which are utilized in translating the grey value image into the binary image as well as in analyzing the edge, the detail of which will be discussed hereinafter.

First Embodiment <FIGS. 1 to 10>

As shown in FIG. 1, the present method utilizes a light source 10 which directs diffused illumination to the surface of an article A in an inclined direction with respect thereto. The article A is shown in the figure to have a defect X with an inclusion Q appearing outwardly adjacent the article A. A TV camera 20 is placed above the article surface with its optical axis extending generally perpendicular to the article surface to capture a two dimensional analog image of a region including the article A. The analog image is then transmitted to an analog-to-digital converter 30 where it is digitized to provide an original grey value image which is stored in an original grey value image memory 51. The original grey value image is composed of a plurality of picture elements or pixels having individual grey values denoting the lightness or darkness of the reflected light from the area including the article surface A.

The original grey value image $I_1$ thus obtained represents, for example, as schematically shown in FIG. 2, the article surface A to be inspected, the defect X within the article surface A, and the inclusion Q. The original grey value image $I_1$ is further processed in a pre-processing section 40 to provide three other images, i.e., an absolute gradient image $I_2$, a directional gradient image $I_3$, and an edge image $I_4$ which are respectively stored in corresponding memories 51 to 54. The edge image $I_4$ is a binary image which is obtained by processing the other three images and which represents, as schematically shown in FIG. 3, edge lines $B_L$, $E_X$, and $E_Q$, respectively indicating border lines of the article surface A, the defect X, and the inclusion Q.

The process of translating the original grey value image $I_1$ into the edge image $I_4$ is based upon the fact that an edge or border line appears between the adjacent pixels showing a remarkable difference in the grey values. Therefore, the edge image $I_4$ is extracted from the original grey value image $I_1$ by differentiating the grey value of each of the pixels in the original grey value image. Such differential processing utilizes, as shown in FIG. 4, a window or square array W of the pixels so as to determine an absolute gradient value [i.e., differential value] as well as a directional gradient value for the center pixel e with respect to eight neighbors a, b, c, d, f, g, h, and i. The absolute gradient value ABs[Pe] and the directional gradient value DEG[Pe] for the pixel e can be defined by the following formulas, respectively:

$$ABS[Pe] = (V^2 + H^2)^{\frac{1}{2}};$$

and $$DEG[Pe] = \tan^{-1} V/H + \pi/2,$$

in which V is the grey value sum of the upper row of the pixels [a, b, c] minus that of the lower row of the pixels [g, h, i], as expressed by the equation;

$$V = (Va + Vb + Vc) - (Vg + Vh + Vi), \text{ and}$$

H is the grey value sum of the left column of the pixels [a, d, g] minus that of the right column of the pixels [c, f, i], as expressed by the equation;

$$H = (Va + Vd + Vg) - (Vc + Vf + Vi);$$

wherein Va, Vb, Vc, Vd, Vf, Vg, Vh, and Vi are grey values of the corresponding pixels a to d, and f to i.

As seen from the above definition, the absolute gradient value ABS[Pe] denotes a maximum grey value gradient that the particular pixel [e] shows in relation to the neighboring pixels, and the directional gradient value DEG[Pe] denotes a direction perpendicular to the direction that the particular pixel [e] shows the maximum grey value gradient.

In this manner, the absolute gradient value and the directional gradient value are obtained for each of the pixels in the original grey value image $I_1$ and are utilized respectively to compose the corresponding images, i.e., the above-mentioned absolute gradient image $I_2$ and the directional gradient image $I_3$.

Then, a thinning operation is added to successively interconnect the pixel to one of the adjacent pixels which has a maximum absolute gradient value relative to the others in such a manner as to draw an edge line having one-pixel width. The resulting edge line can be regarded as a ridgeline RL extending along a curved surface of the absolute differential value image $I_1$, as shown in FIG. 5 in which the corresponding pixels are arranged in X-Y directions and the absolute gradient values of the pixels are plotted in Z direction. So far, every edge line or ridge line is extracted irrespective of whether the absolute gradient values are large or small. However, thus extracted edge lines may involve or reflect permissible error resulting from a noise, and therefore only the edge lines are extracted which trace the gradient values exceeding a suitable threshold THL, as shown in FIG. 6, for elimination of the noise effect. The edge line thus obtained may sometimes become incontinuous as a result of that the original grey value image includes poor contrasted regions or suffers from a considerable amount of noises. For compensation of this, an edge elongation technique is utilized to provide a non-interrupted edge line. The technique comprises to locate an interrupted point of the edge line, elongate the edge line in such a direction of obtaining a greatest value by an evaluation function as expressed by the following equation:

$$f[P_j] = ABS[P_j] \cdot \cos(DEG[P_j] - DEG[P_o]) \cdot \cos((j-1)/4 - DEG[P_o]),$$

in which $ABS[P_j]$ denotes the absolute gradient value assigned to ones of the 8 (eight) neighboring pixels $[P_j]$ surrounding the pixel $[P_o]$ corresponding to the interrupted point [i.e., j indicates 1 to 8], while $DEG[P_j]$ and $DEG[P_o]$ represent respectively the directional gradient values assigned to ones of the eight surrounding pixels and to the pixel corresponding to the interrupted point. That is, the evaluation function is applied to each one of the 8 (eight) neighboring pixels surrounding one particular pixel at the interrupted point of the edge line in order to locate one of the surrounding pixels which has a greatest evaluation function value, whereby the edge line is elongated from the interrupted point toward that pixel. The above operation continues until the edge line is elongated to reach the interrupted end of the adjacent edge line.

The edge image $I_4$ thus obtained through the above processing is stored together with the original grey value image $I_1$, absolute gradient image $I_2$, directional gradient image $I_3$ in the corresponding memories 51 to 54. It should be noted at this time that these images are composed of the individual pixels and that the pixels in the original grey value image $I_1$ correspond in one-by-one relation to the individual pixels in the other three images $I_2$ to $I_4$. In the following description, the pixels of the four different images are denoted by X-Y coordination system so that and the values at a given pixel for the original grey value image, absolute gradient image, directional gradient image, and edge image are respectively denoted by $f_1(x,y)$, $f_2(x,y)$, $f_3(x,y)$, and $f_4(x,y)$. In the present embodiment, the grey values $f_1(x,y)$ of the original grey value image is defined by an 8-bit word so that the grey value $f_1(x,y)$ can have 0 to 255 levels of lightness. The absolute gradient value $f_2(x,y)$ is defined by a 6-bit word and therefore can have 0 to 63 levels. The directional gradient value $f_3(x,y)$ is defined by a 4-bit word and can be associated to one of 16 directions. The value $f_4(x,y)$ of the edge image is defined by a single bit and can have either "1" or "0" forming the edge line or not. As usual in describing the lightness or darkness by means of the grey values, the grey value in the description of the present invention is defined to increase with increasing lightness.

After the above pre-processing is completed and the individual images are stored in the memories 51 to 54, the edge image $I_4$ is accessed in accordance with a programmed routine as shown in FIG. 7. Firstly, the routine addresses a scan processing section 60 in FIG. 1 to provide a search track S within the confines of the border line BL of the article surface. The search track S is defined as a closed loop having a common start and end point CP of search and may have any configurations, for example, as shown in FIGS. 9A to 9D. Then, the program proceeds to trace the search track S from the start point CP to seek a point where $f_4(x,y)=1$, i.e., the pixel where the search track S firstly encounters the edge $E_x$ of the defect, and designate that point or pixel as a flag point F.

Figure 8:
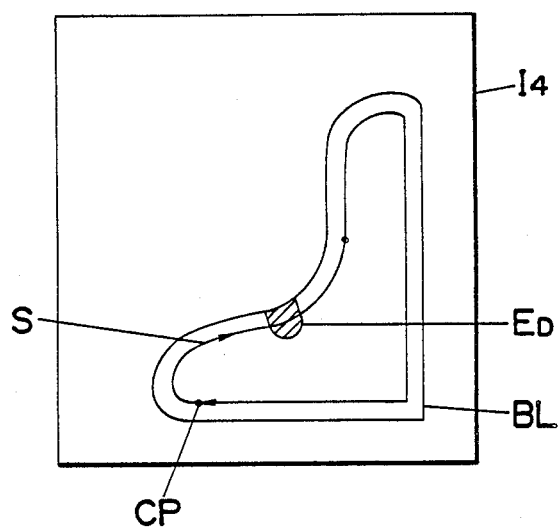
FIG. 8 illustrates a manner of scanning the edge image along a search track for detecting an edge according to the first embodiment.
Figure 9A:
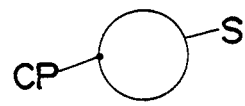
FIG. 9, composed of FIGS. 9A to 9D, illustrates several forms of search tracks which may be utilized in the scanning for the edge.
Figure 9B:
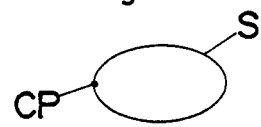
Figure 9C:
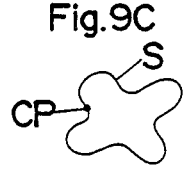
Figure 9D:
Figure 10:
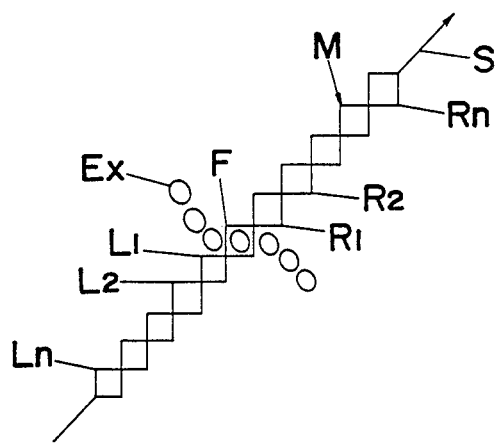
FIG. 10 illustrates a set of the pixels forming a mask and arranged on the search track on the opposite sides of the edge line.

Next, a mask processing section 70 is called to define an extended mask M of the pixels $L_1$ to $L_n$, F, and $R_1$ to $R_n$ in the edge image $I_4$ which, as indicated by hatched lines in FIG. 8, are selected to arrange along the search track S on the opposite sides of the flag point F. The mask M covers the $(2n+1)$ pixels with at least two pixels disposed symmetrically on either side of the flag point F. The individual pixels $L_1$ to $L_n$, and $R_1$ to $R_n$ in the above mask M in the edge image $I_4$ can be designated by using the common X-Y coordinate system as $L_1(X_{F-1}, Y_{F-1})$ to $L_n(X_{F-n}), F(X_F, Y_F)$ and $R_1(X_{F+1}, Y_{F+1})$ to $R_n(X_{F+n}, Y_{F+n})$. At a grey value processing section 80, the corresponding pixels in the original grey value image $I_1$ are selected in order to calculate a sum D of an individual grey value difference between the pixels in each symmetrical pair, the sum D being expressed by the following equation:

$$D = \Sigma |L_i(X_{F+i}, Y_{F+i}) - R_i(X_{F-1}, Y_{F-1})|$$

in which $i=1, 2, \ldots, n$ or $i=m, m+1, \ldots n$ ($m>1$), wherein n and m are integers. The sum D is compared at an evaluation processing section 90 with a predetermined threshold $TH_1$ to judge that the above flag point F on the search track S is truly indicative of the defect X when the sum D exceeds the threshold $TH_1$. This is based upon the recognition that the mask M straddles the edge $E_x$ of the defect X to extend over non-defective region and defective region and therefore that the sum D is well indicative of a critical grey value difference between these two contrasted regions. Further, since the sum D takes into account the grey value difference for more than one symmetrical pair of the pixels extending further into the defective and non-defective regions, it is possible to enhance the contrast between the two regions on the opposite sides of the edge or the flag point F, improving inspection reliability and accuracy.

When the sum D is found not to exceed the threshold $TH_1$, the process continues to trace the search track S toward its end point for detection of another flag point on the track S. When no flag point is detected or any flag point is evaluated to give the sum D not exceeding the threshold $TH_1$, it is judged that no defect is detected on the search track S.

Figure 11:
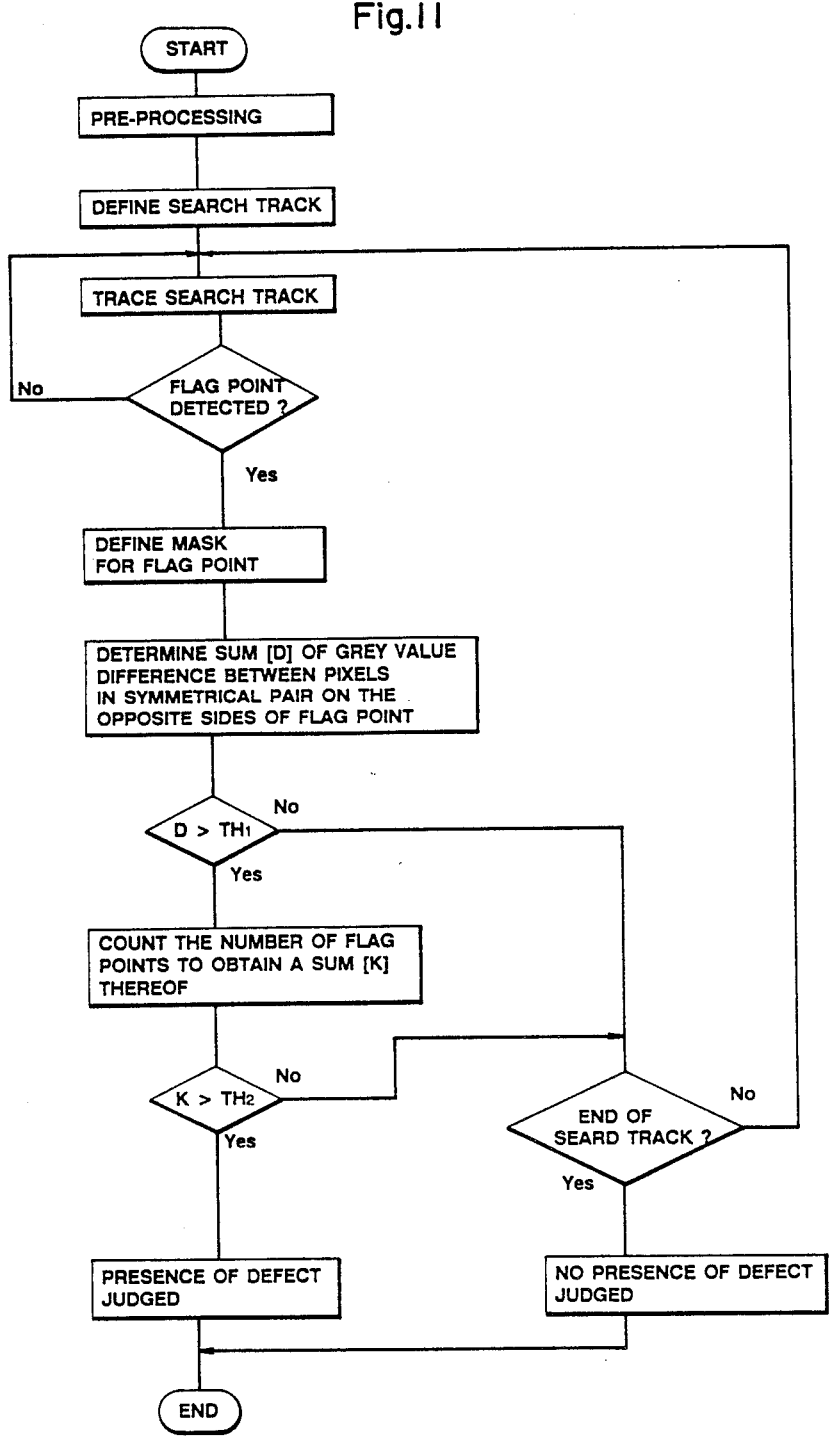
FIG. 11 is a flow chart of the optical surface inspection system in accordance with a second embodiment of the present invention.
Figure 12A:
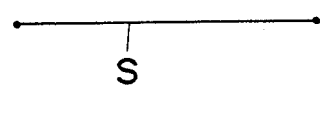
FIG. 12, composed of FIGS. 12A to 12D, illustrates several forms of search tracks which may be utilized in the scanning for the edge according to the second embodiment.
Figure 12B:
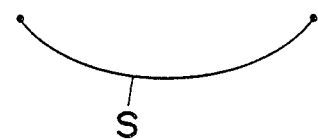
Figure 12C:
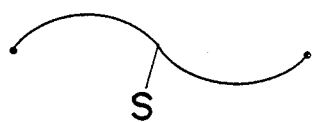
Figure 12D:
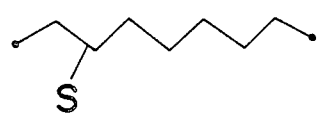

Second Embodiment <FIGS. 11 and 12>

A second embodiment is basically similar to the first embodiment except that it utilizes a search track S which has its starting and ending points spaced apart. The search track S is locally defined within the border line of the article surface in the edge image and may take the form of a straight, curved, meandering line, for example, as shown in FIGS. 12A to 12D. The same processing are utilized as in the first embodiment to detect a flag point F on the search track S, to define a corresponding mask M of the pixels in the edge image, and to obtain a like sum D of the individual grey value difference between the pixels in each symmetrical pair in the mask M.

In this embodiment, the flag point F or the mask M is designated as a defect indicative one when the sum D exceeds the above threshold $TH_1$. In this way, all the flag points detected along the entire search track S are evaluated whether they could be designated as the defect indicative points. Then, the total number K of the defect indicative points is compared with a predetermined threshold $TH_2$ to thereby judge the presence of a defect on the search track S when $K > TH_2$. The evaluation routine of the present embodiment is shown in FIG. 11. As apparent from the above, a more strict and reliable determination of the defect is possible in the present embodiment.

Figure 13:
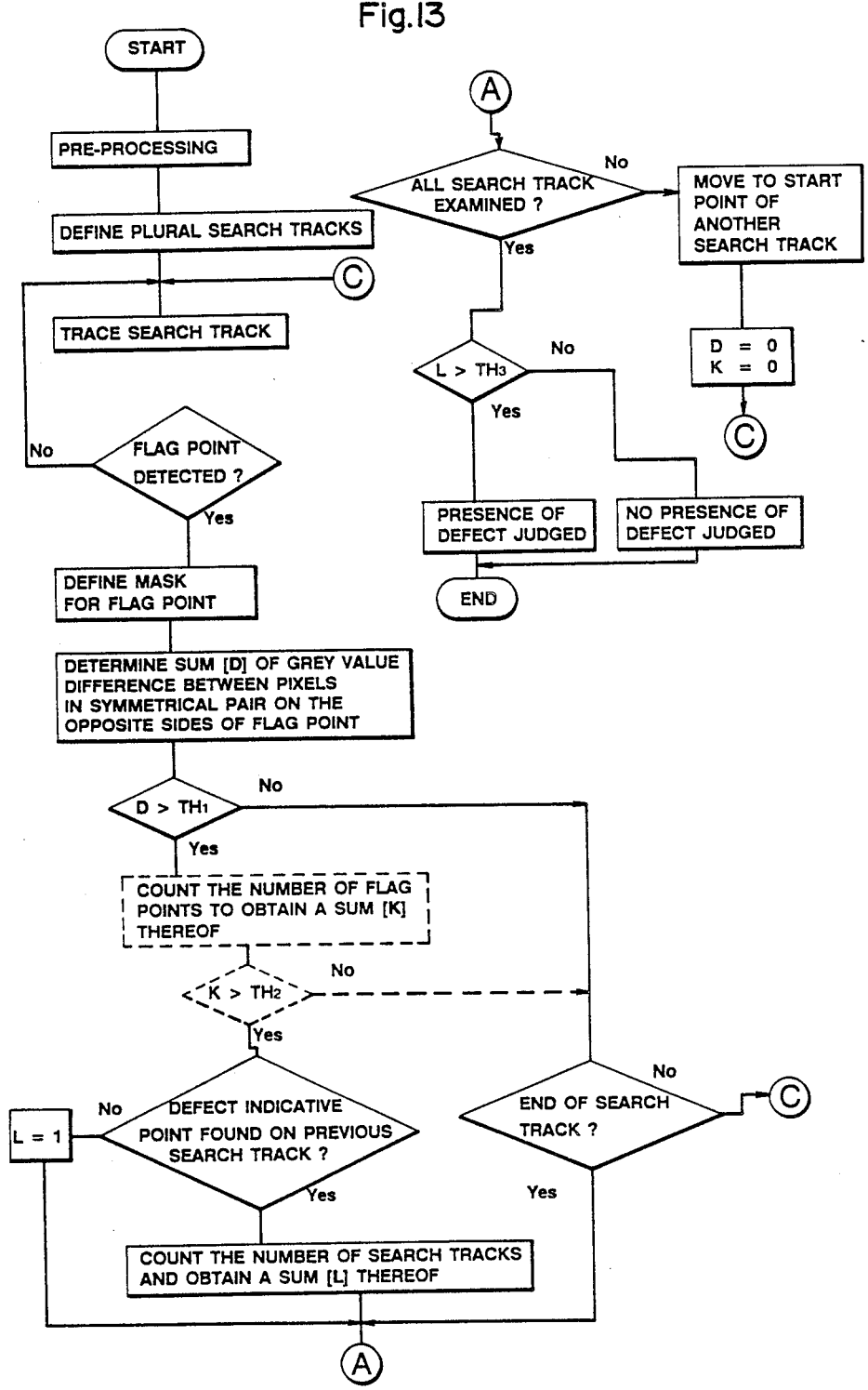
FIG. 13 is a flow chart of the optical surface inspection system in accordance with a third embodiment of the present invention.
Figure 14:
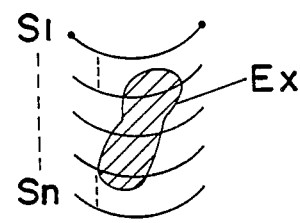
FIG. 14 illustrates a set of search tracks provided for detection of an edge of a defect according to the third embodiment.

Third Embodiment <FIGS. 13 and 14>

FIG. 13 illustrates a programmed routine for defect evaluation in accordance with a third embodiment of the present invention. As shown in FIG. 14, the present embodiment utilizes a plurality of generally parallel search tracks $S_1$ to $S_n$ which are defined within the border line of the article surface in the edge image. Each of the search tracks $S_n$ is scanned and is designated as a defect indicative line when it is evaluated to have a defect in the manner as employed in the first or second embodiment. Defect evaluation of the present embodiment is then made to determine the number L of the successive or adjacent search tracks which are each designated as the defect indicative line, and to compare the number L of that lines with a predetermined threshold $TH_3$, whereby judging the presence of a defect when $L > TH_3$. The programmed routine of FIG. 13 is illustrated to include, for designation of the defect indicating line, the steps of the detect evaluation process employed in the second embodiment which are shown in dotted boxes. Therefore, by omitting the steps in the dotted boxes, the programmed routine of FIG. 13 can be converted to utilize the steps of the detect evaluation employed in the first embodiment for designation of the defect indicating line.

Fourth Embodiment <FIGS. 15 to 18>

Figure 16:
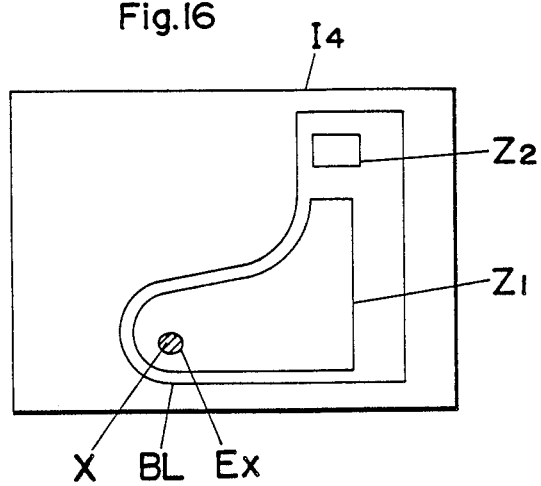
FIG. 16 is a schematic view of an edge image to be scanned for detection of an edge according to the fourth embodiment.

A fourth embodiment of the present invention utilizes the same pre-processing as in the first embodiment to acquire an original grey value image and an edge image of a region including the surface area to be inspected. Subsequent to the pre-processing, an inspection zone $Z_1$ is defined within the border line BL of the article surface in the edge image $I_4$, as shown in FIG. 16. Also, a reference zone $Z_2$ is separately defined within the border line BL. These zone $Z_1$ and $Z_2$ are suitable selected in accordance with a known pattern or design of the article surface intended to be inspected.

Figure 15:
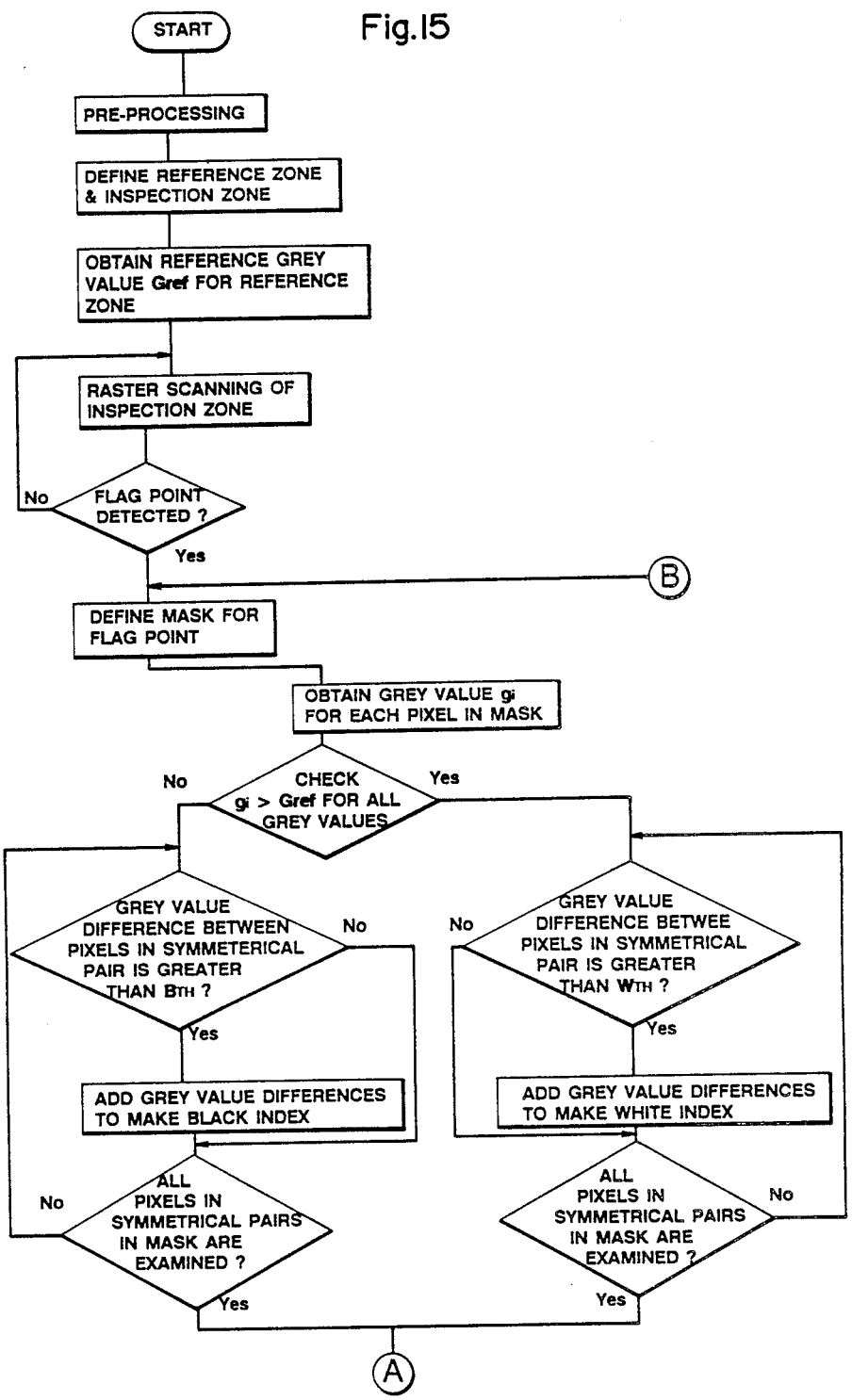
FIG. 15 is a flow chart of the optical surface inspection system in accordance with a fourth embodiment of the present invention.
Figure 15:
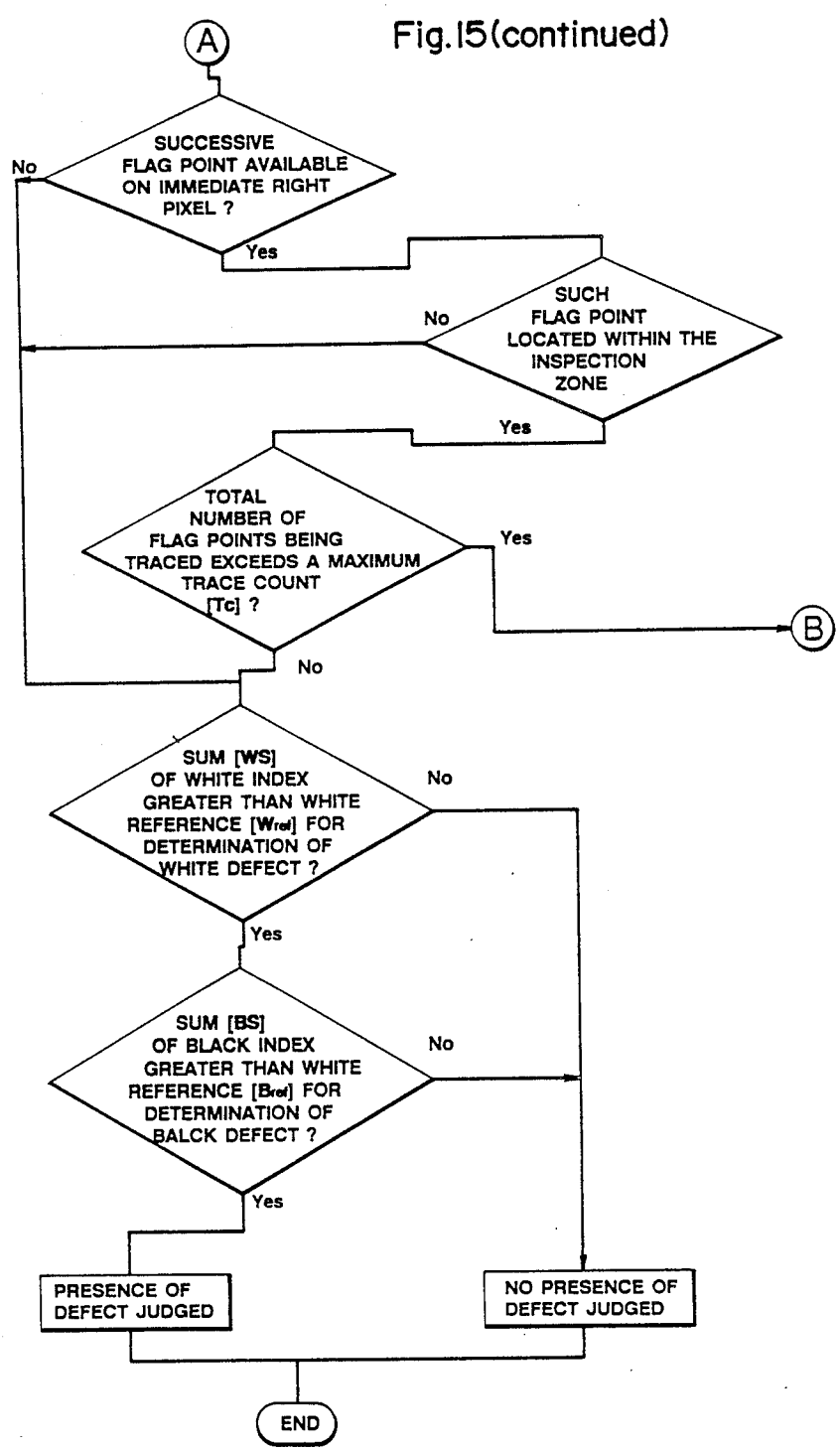
Figure 17:
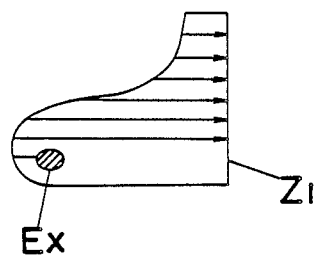
FIG. 17 is a schematic view of an inspection region in the edge image of FIG. 16.

Evaluation process of the present embodiment is performed in a programmed manner as illustrated in FIG. 15. In the first step, a reference grey value $G_{ref}$ is calculated which is an average of the grey levels of all the pixels in the original grey value image $I_1$ corresponding to those located within the reference zone $Z_2$. Then, the inspection zone $Z_1$ is analyzed by raster scanning, as shown in FIG. 17, to detect a point where $f_4(x,y) = 1$, or the pixel at which the scan line firstly encounters the edge $E_x$ of a defect X. The pixel which is firstly detected as indicating the edge is designated as an initial flag point $F_0$ of which coordinates can be denoted as $(x_0, y_0)$. Further, the pixels forming that edge are traced and designated as successive flag points which define with the initial flag point a series of flag points $F_0$ to $F_i$ arranged along the edge direction.

Figure 18:
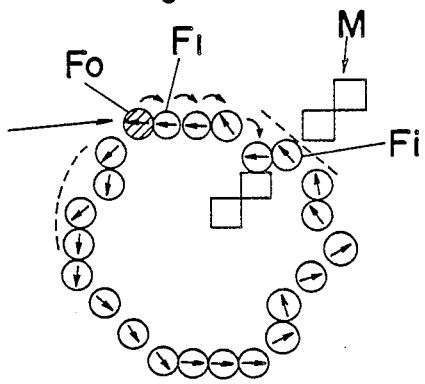
FIG. 18 is a schematic view illustrating a series of flag points determined for the pixels arranged along the edge line with one of masks of the pixels shown to arrange in a direction normal to the edge direction.

With regard to thus defined series of flag points, analysis is made firstly to the initial flag point $F_0(x_0,y_0)$ and successively to the adjacent pixels $Fn(x_n,y_n)$ arranged in a clockwise direction, as shown in FIG. 18. The analysis for a given flag point $F_i(x_i, y_i)$, where i denotes an integer, comprises the following steps. Firstly, a directional gradient value $f_3(x_i, y_i)$ is derived from the image $I_3$ in the memory 53 in correspondence to the given flag point $F_i(x_i, y_i)$. Based upon the directional gradient value $f_3(x_i, y_i)$, a mask M is defined to include the pixels arranged in a direction perpendicular to the direction determined by that direction value (indicated by an arrow in a circle in FIG. 18). In this embodiment, the pixels defining the mask M are those arranged symmetrically on the opposite sides of the flag point $F_i (x_i, y_i)$ and spaced therefrom respectively by m-pixel and n-pixel distances, and can be expressed by the respective coordinates of $(x_{i+m}, y_{i+m})$, $(x_{i+n}, y_{i-n})$, $(x_{i-n}, y_{i-n})$, and $(x_{i-m}, y_{i-m})$. The grey values of the corresponding pixels in the original grey value image $I_1$ are obtained and denoted respectively as $g_1$, $g_2$, $g_3$, and $g_4$, as below:

$$g_1 = f_1(x_{i+m}, y_{i+m});$$

$$g_2 = f_1(x_{i+n}, y_{i+n});$$

$$g_3 = f_1(x_{i-n}, y_{i-n});$$

and $$g_4 = f_1(x_{i-m}, y_{i-m}).$$

In the next step, the respective grey values $g_1$, $g_2$, $g_3$, $g_4$ are each compared with the above reference grey value $G_{ref}$ to see whether the defect is a lighter one (hereinafter referred to simply as a white defect) having a greater grey value or dark one (hereinafter referred to simply as a black defect) having a less value than the reference zone $Z_2$. When all of the pixels defined by the mask M have the grey values $g_1$, $g_2$, $g_3$, and $g_4 > G_{ref}$, the defect is presumed as the white defect and a white threshold $W_{th}$ is utilized for subsequent evaluation of the defect. Otherwise, that is, any one of these pixels has the grey value less than the reference grey value $G_{ref}$, the defect is presumed as the black defect and a black threshold $B_{th}$ is utilized for the subsequent evaluation. The white and black threshold $W_{th}$ and $B_{th}$ are suitably selected in consideration of an expected nature of defects. When the defect is presumed as the white one, each symmetrical pair of the pixels defined in the mask M is examined whether the grey value difference between the pixels in the symmetrical pair is greater than the white threshold, i.e., $|g_1 - g_4| > W_{th}$, and $|g_2 - g_3| > W_{th}$. The grey value difference whichever greater than $W_{th}$ is sampled as a white index. On the other hand, when the defect is presumed as the black one, each symmetrical pair of the pixels defined in the mask M is examined in the like manner to satisfy the followings, $|g_1 - g_4| > B_{th}$ or $|g_2 - g_3| > B_{th}$. The grey value difference whichever greater than $B_{th}$ is sampled as a black index.

After obtaining the white or black index for the mask M defined around the given flag point $F_i$, the process continues to trace the adjacent flag point $F_{i+1}$, define the like mask, and obtain a corresponding white or black index for that mask. This process terminates when either of the following conditions is met:
(1) the number of the flag points having been traced exceeds a predetermined maximum trace count $T_c$;
(2) the flag point extends out of the inspection zone $Z_1$; or
(3) no adjacent flag point is found within the inspection zone $Z_1$.

The white and black indexes thus obtained for the individual flag points or masks are totalized respectively to provide an individual white sum WS and a black sum BS, which are then respectively compared with predetermined white reference $W_{ref}$ and black reference $B_{ref}$. Finally, it is judged that the inspection zone $Z_1$ sees the true presence of the white defect when $W_s > W_{ref}$, and the true presence of the black defect when $B_s > B_{ref}$. The white and black thresholds and references $W_{th}$, $B_{th}$, $W_{ref}$, $B_{ref}$, and the maximum trace count $T_c$ are suitably selected in accordance with an expected nature of the defects.

After completing the evaluation of the defect with regard to the series of flag points and no defect is judged, the above evaluation process is repeated to another series of flag points defined within the inspection zone $Z_1$.

Figure 19:
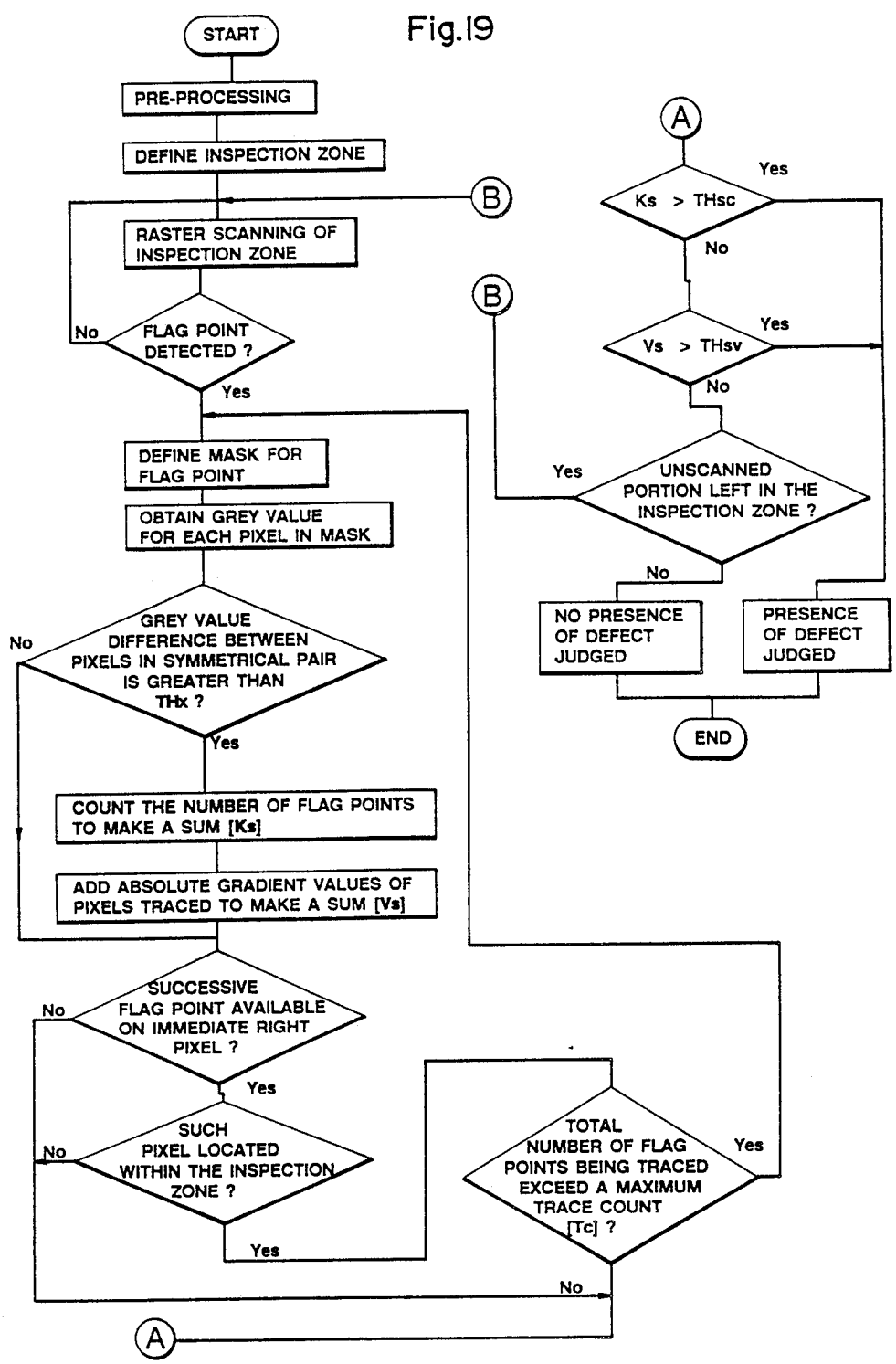
FIG. 19 is a flow chart of the optical surface inspection system in accordance with a fifth embodiment of the present invention.

Fifth Embodiment <FIG. 19>

In a fifth embodiment of the present invention which also utilize the like pre-processing to provide an original grey value image and a corresponding edge image, only an inspection zone is defined within the border line of the article surface in the edge image. The inspection zone is analyzed, in the same way as in the fourth embodiment, by raster scanning in order to detect a series of flag points, define an individual mask corresponding to each of the flag points starting from the initial flag point, and obtain the grey values $g_1$, $g_2$, $g_3$, and $g_4$ for the pixels forming the two symmetrical pairs in each mask. The grey value differences $|g_1 - g_4|$ and $|g_2 - g_3|$ respectively between the pixels in the symmetrical pairs of the mask are compared with a predetermined threshold $TH_x$ to see whether either of the following inequalities is satisfied:

$$|g_1 - g_4| > TH_x; \text{ or}$$

$$|g_2 - g_3| > TH_x.$$

The tracing of the flag points and the termination of the tracing are made in the same way as in the fourth embodiment. The above evaluation is made for each of the masks defined respectively around the flag points which have been traced in such a way as to count the number of the flag points or masks that satisfy either of the above inequalities, and to provide a sum count $K_s$ for all the flag points having been traced. Further, with regard to all the flag points or the pixels having been traced, the corresponding absolute gradient values are derived from the image $I_2$ in the memory 52 and are added together to provide a sum value $V_s$. The sum count $K_s$ and the sum value $V_s$ are compared respectively with predetermined threshold number and value $TH_{sc}$ and $TH_{sv}$ such that a defect is judged to be seen in the inspection zone when either of the following inequalities is satisfied:

$$K_s > TH_{sc}; \text{ or}$$

$$V_s > TH_{sv}.$$

When no defect is judged for the first series of the flag points, the above evaluation is repeated to another series of the flag points in the remaining region within the inspection zone which have not yet been scanned. After the entire inspection zone is scanned and no flag point is detected or either of the above inequalities is not satisfied for any series of the flag points, the inspection zone is judged to include no actual surface defect. The evaluation process of this embodiment is illustrated in FIG. 19.

Figure 20:
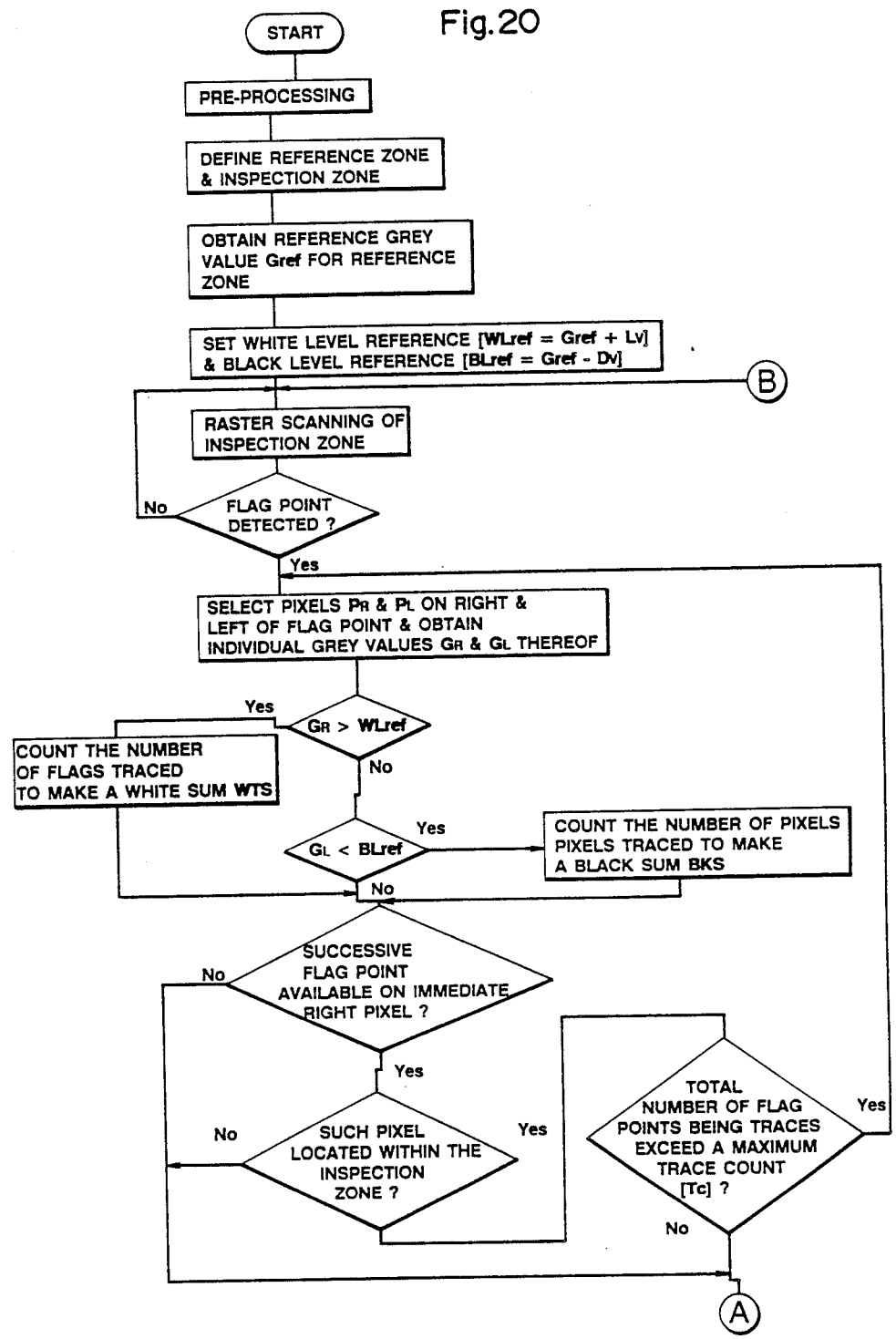
FIG. 20 is a flow chart of the optical surface inspection system in accordance with a sixth embodiment of the present invention.
Figure 20:
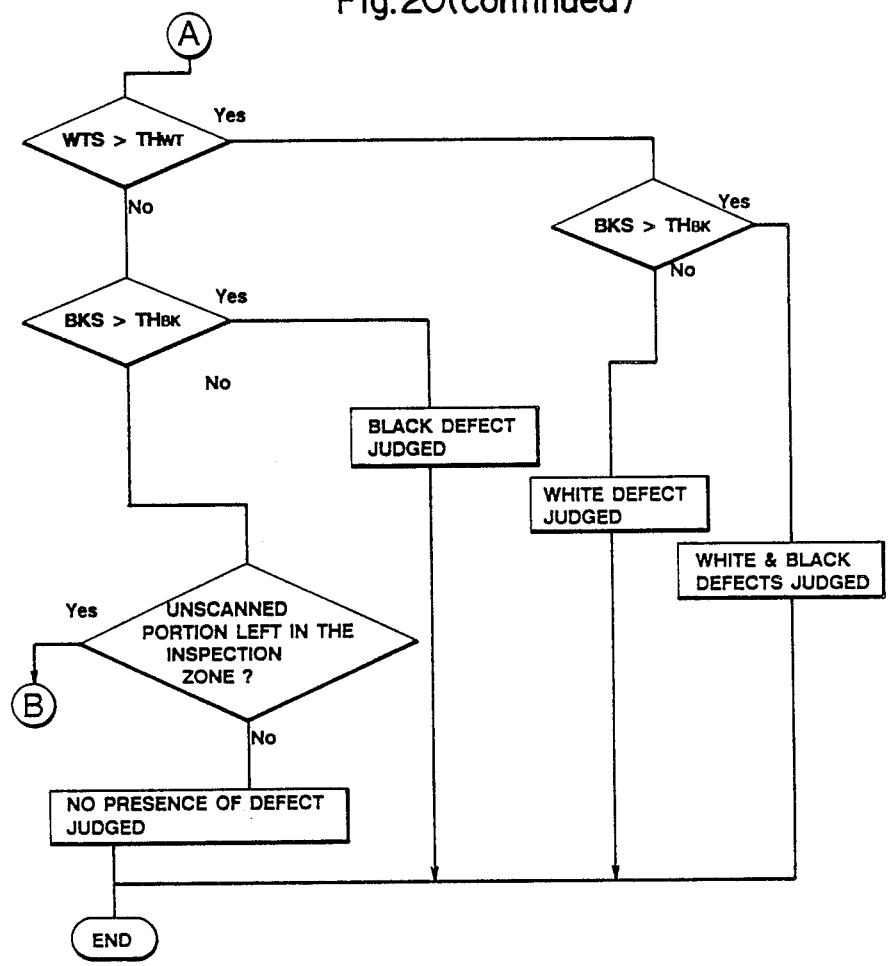
Figure 21:
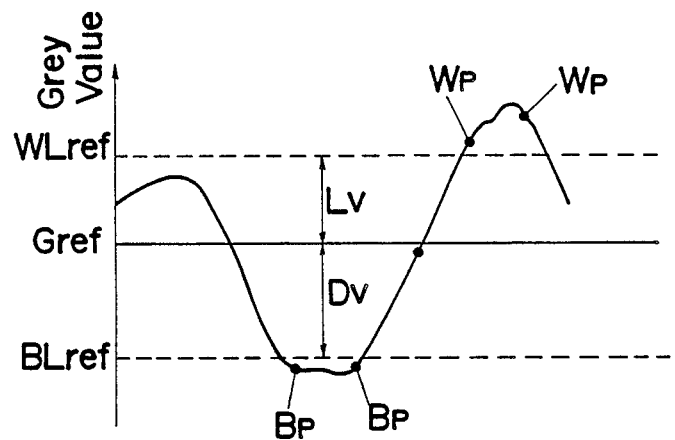
FIG. 21 illustrates the relationship among three threshold values utilized in the sixth embodiment for evaluation of the presence of a defect.

Sixth Embodiment <FIGS. 20 and 21>

In the like manner as in the fourth embodiment, the present embodiment provides a like reference zone $Z_2$ together with a like inspection zone $Z_1$ within the border line of the article surface in the edge image $I_4$. The grey values of the pixels composing the reference zone $Z_2$ are averaged to obtain a grey level reference $G_{ref}$ from which a white level reference $WL_{ref}$ and a black level reference $BL_{ref}$ are set for analysis of whether the defect is lighter one [white defect] or darker one [black defect]. To this end, the white level reference $WL_{ref}$ and the black level reference $BL_{ref}$ are set to be greater and smaller than the reference grey level $G_{ref}$ respectively by offset values $L_v$ and $D_v$, as follows:

$$WL_{ref} = G_{ref} + L_v;\text{ and}$$

$$BL_{ref} = G_{ref} - D_v.$$

Figure 22:
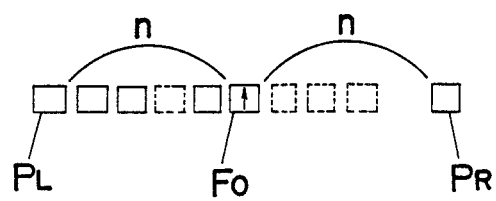
FIG. 22 is a schematic view illustrating the selected pixels in an edge image for defect evaluation in accordance with the sixth embodiment.

As illustrated in the program of FIG. 20, the next step is to scan the inspection zone $Z_1$ in the same way as in the fourth embodiment in order to determine an initial flag point $F_0$ of the pixel in the edge image. Thereafter, two pixels $P_L$ and $P_R$ are selected which are, as shown in FIG. 22, disposed symmetrically on the opposite sides of the flag point $F_0$ along a direction perpendicular to the direction (shown by a small arrow in a box) defined by the above-mentioned directional gradient value of the pixel corresponding to the flag point $F_0$, and which are spaced apart from the flag point $F_0$ by a n-pixel distance. As apparent from its definition, the above directional gradient value indicates such a direction that has a light area on the righthand side thereof and a dark area on the lefthand side thereof. Accordingly, the pixel $P_R$ on the right hand of the flag point $F_0$ is deemed to correspondingly have the grey value $G_R$ greater than the grey value $G_L$ of the left pixel $P_L$. Based upon this understanding, these grey values $G_R$ and $G_L$ are compared respectively with the above white and black level references $WL_{ref}$ and $BL_{ref}$, thereby determining the flag point $F_o$ as a white defect indicative point $W_p$ when $G_R > WL_{ref}$ and as a black defect indicative point $B_p$ when $G_L < BL_{ref}$, as shown in FIG. 21.

In the next step, ones of the other pixels forming the series of flag points are successively traced, in the like manner as in the fourth embodiment, during which the above analysis is repeated in order to count the number of the white and black defect indicative points $W_p$ and $B_p$ for obtaining a white sum WTS and a black sum BKS. The above tracing of the flag points is subject to the same terminating condition as employed in the fourth embodiment. Upon termination of the flag point tracing, the individual sums WTS and BKS of the white and black defect indicative points are compared respectively with predetermined white and black thresholds $TH_{WT}$ and $TH_{BK}$. Then, it is finally judged that the inspection zone $Z_1$ sees the defect when either of the following inequalities is satisfied:

$$WTS > TH_{WT}, \text{ or}$$

$$BKS > TH_{BK}.$$

When neither of the above inequalities is satisfied, then the above evaluation process is repeated as to the remaining region which has not been scanned within the inspection zone $Z_1$. When no flag point is detected or no condition is seen to satisfy either of the above inequalities after scanning the entire inspect region $Z_1$, it is judged that the inspection zone $Z_1$ is free from a defect.

Figure 23A:
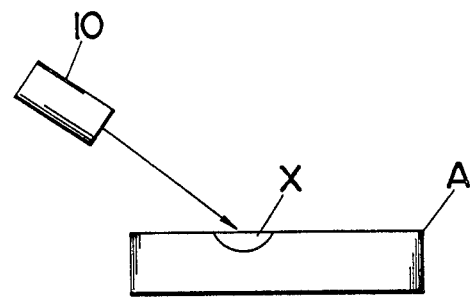
FIGS. 23A and 23B are respectively schematic elevational and plan views of the article surface in relation to the illuminating direction from a light source in accordance with a seventh embodiment of the present invention.
Figure 23B:
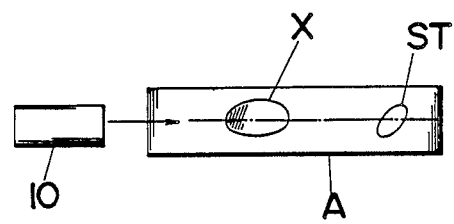
Figure 24:
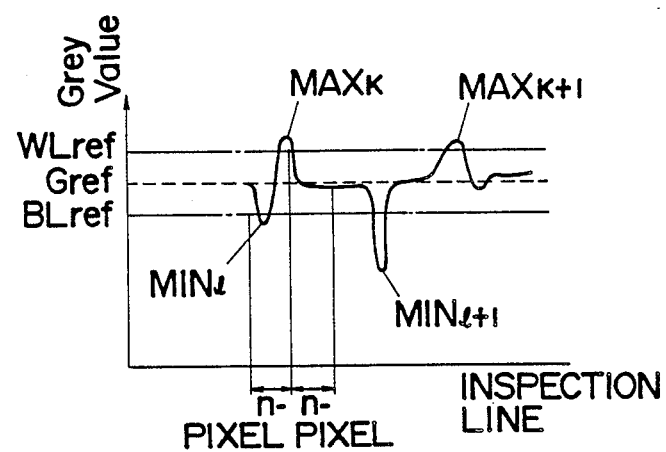
FIG. 24 is a graphical representation of a grey value distribution of the grey value image of the article surface taken along the illuminating direction according to the seventh embodiment.
Figure 25:
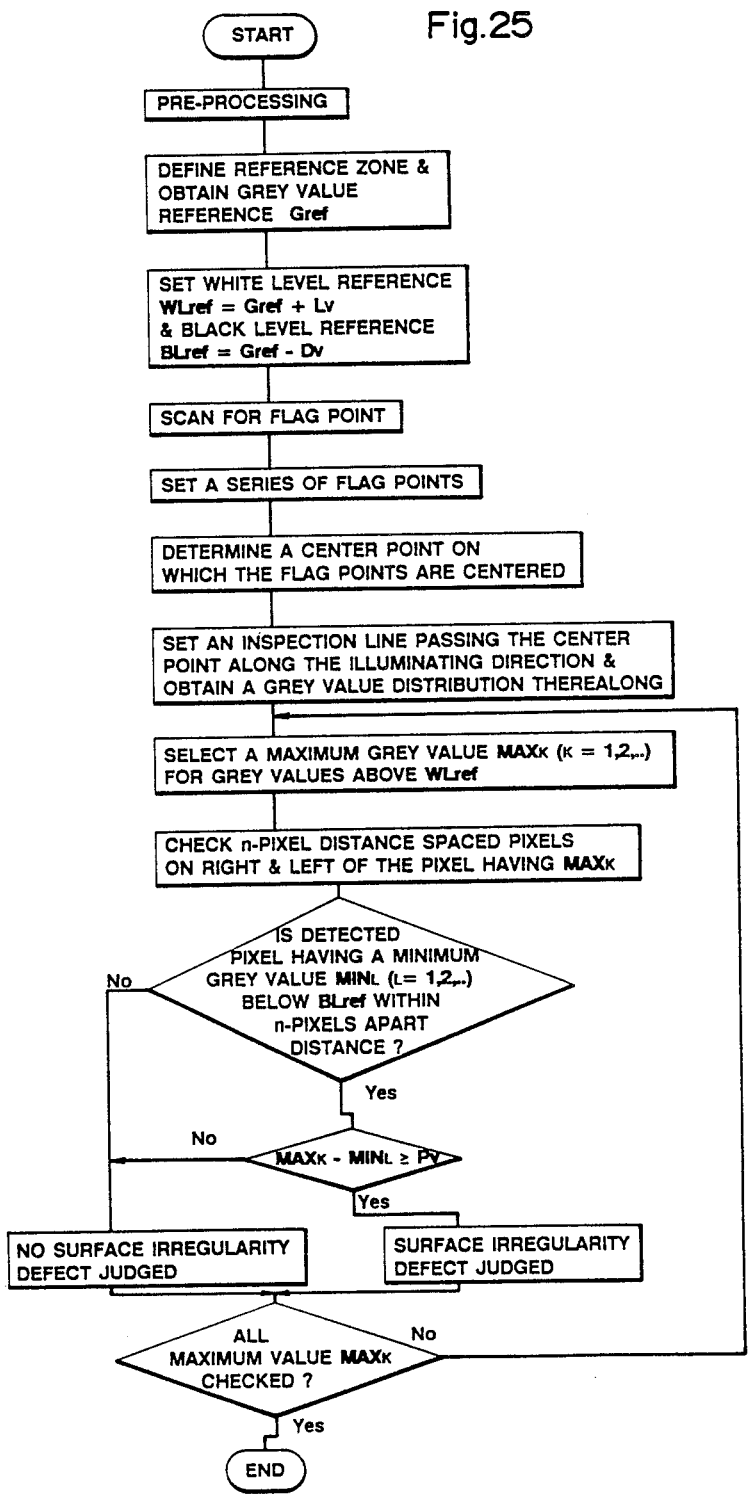
FIG. 25 is a flow chart of the optical surface inspection system according to the seventh embodiment.

Seventh Embodiment <FIGS. 23 to 25>

A seventh embodiment of the present invention is directed to a further imposed evaluation process capable of well discriminating a defect X of surface irregularity. Such surface irregularity includes, for example, a tiny projection or depression appearing on or in the article surface, or even a large projection or depression which is relatively large but inclined at a small angle with respect to the general surface of the article A such that it only causes a poor contrast in relation to the normal region in the original grey value image when the article A is illuminated from the direction inclined with the article surface, as shown in FIG. 23A.

The present embodiment utilizes the similar pre-processing as in the first embodiment to provide a original grey image and an edge image of a region including the article surface. Further, a reference zone is suitably selected within the article surface so as to provide a like grey value reference $G_{ref}$, a like white level reference $WL_{ref}(=G_{ref}$ plus an offset value $L_v$), and a black level reference $BL_{ref}(=Gref$ minus an offset value $D_v$), as determined in the sixth embodiment. That is, the grey value reference $G_{ref}$ is determined as an average of the grey values of the pixels forming the reference zone so that it can compensate for variations in the illumination level and in the surface characteristic of the article being inspected, thereby making the above references consistent for evaluation of the defect.

Referring to the programmed routine of FIG. 25, the next step is to scan the edge image for detection of a point of an edge indicative of the defect. Upon initial detection of that point (which is designated as an initial flag point), another scan is made to trace along the edge from the initial flag point to find a series of the pixels forming the edge, which pixels are arranged in adjacent relation along the edge and designated as a series of flag points. Then, it is determined a center point on which the series of the flag points are substantially centered. Based upon the x-y coordinates of the center point thus determined, the original grey value image is processed to present a grey value distribution along an inspection line which passes the pixels corresponding to the center point and extends along the above illuminating direction.

The grey value distribution thus obtained represents, as shown in FIG. 24, varying amplitudes of the grey values of the pixels arranged along the inspection line.

As seen in the figure, the grey value distribution may include plural sets of the successively appearing grey values exceeding the above white level reference $WL_{ref}$ and plural sets of the grey values falling below the above black level reference $BL_{ref}$. Firstly, a maximum grey level $MAX_k$ (where k is an integer) is determined to each set of the grey values above the white level reference $WL_{ref}$ and a minimum grey level $MIN_l$ (where 1 is an integer) is determined to each set of the grey values below the black level reference $BL_{ref}$. Then, for each maximum grey level $MAX_k$, analysis is made as to whether there is, within n-pixel distance on the opposite sides of the pixel having maximum grey level $MAX_k$, a pixel having the minimum grey level $MIN_l$. If so found, a grey value difference $G_{DEF}$ is calculated between the maximum grey value $MAX_k$ and the minimum grey value $MIN_l$, and is compared with a predetermined value $P_v$ to thereby judge the presence of a defect having surface irregularity when $MAX_k - MIN_l \geq P_v$. Otherwise, the same evaluation is made to another maximum grey value $MAX_{k+1}$, if present. It is noted at this time that, as shown in FIG. 24, the defect such as a stain ST resulting from other than the surface irregularity causes a characteristic pattern of the grey values along the reference line in which only minimum grey value $MIN_{l+1}$ appears without accompanied by associated maximum grey value as defined. Therefore, such defect ST other than the surface irregularity can be discriminated from the defect indicative of the surface irregularity in the above evaluation, and may be reliably detected by suitably analyzing the above characteristic pattern. When no surface irregularity defect is judged with regard to the series of the flag points, the same procedure is repeated for another series of the flag points in the like manner as in the sixths embodiment.

What is claimed is:

1. An optical surface inspection method for inspecting a surface defect such as a crack, stain, and irregularity of an article, said method comprising the steps of:
    illuminating said article surface;
    acquiring an original grey value image of an illuminated region including said article surface, said original grey value image comprising a number of pixels having individual grey values;
    processing said original grey value image so as to determine, for each of said pixels in said original grey value image, a maximum absolute gradient of the grey values relative to the neighboring pixels, to provide an absolute gradient image having a corresponding number of pixels each having thus determined maximum absolute gradient of the grey level, and to convert said absolute gradient image into an edge image, said edge image comprising a number of corresponding pixels having binary values representing a border line of said article surface and an edge indicative of a possible defect within said border line;
    providing at least one search track within the confines of said border line;
    tracing along said search track to find a flag point at which said search track transverses said edge; selecting a plurality of said pixels in the vicinity of said flag point; and
    analyzing the grey values of the pixels in the original grey value image which correspond to said selected pixels in the edge image as to whether there is a critical change in the grey values, whereby judging that said edge is indicative of a defect by that critical change in the grey values.

2. A method as set forth in claim 1, wherein said selected pixels are arranged along said search track and symmetrically on the opposite sides of said flag point to define an extended mask including more than one symmetrical pair of said pixels; and wherein said analyzing step comprises sub-steps of:
    determining, in accordance with the corresponding pixels in said original grey value image, an individual difference between the grey values of said pixels in said each symmetrical pair;
    summing said individual grey value differences determined for all of said symmetrical pairs in said mask to obtain a sum grey value difference;
    comparing said sum grey value difference with a predetermined reference value for evaluation of said critical change.

3. A method as set forth in claim 1, wherein said selected pixels are arranged along said search track and symmetrically on the opposite sides of said flag point to define an extended mask including more than one symmetrical pair of said pixels; and wherein said analyzing step comprises sub-steps of:
    determining, in accordance with the corresponding pixels in said original grey value image, an individual difference between the grey values of said pixels in said each symmetrical pair;
    summing said individual grey value differences determined for all of said symmetrical pairs to obtain a sum grey value difference;
    comparing said sum grey value difference with a predetermined reference value to designate said flag point as a defect indicative point when said sum grey value difference is above said reference value;
    comparing the number of said defect indicative points determined on said search track with a predetermined reference number for evaluation of said critical change such that the a defect is judged to be present on said search track when the number of said defect indicative points exceeds said predetermined number.

4. A method as set forth in claim 1, wherein a plurality of said search tracks are provided within the confines of said border line of said article surface to be traced successively, and said selected pixels are arranged along said search track and symmetrically on the opposite sides of said flag point to define an extended mask including more than one symmetrical pair of said pixels; and wherein said analyzing step comprises sub-steps of:
    determining, in accordance with the corresponding pixels in said original grey value image, an individual difference between the grey values of said pixels in said each symmetrical pair;
    summing said individual grey value differences determined for all of said symmetrical pairs in each mask to obtain a sum grey value difference;
    comparing said sum grey value difference with a predetermined reference value to designate said search track as a defect indicative track when said sum grey value difference is above said reference value;
    successively tracing another one of said search tracks to determine whether said another search track is designated as said defect indicative track;
    judging that the presence of a defect when the said defect indicative tracks are designated successively for the adjacent ones of said search tracks and the number of said defect indicative tracks exceeds a predetermined number.

5. A method as set forth in claim 1, wherein a plurality of said search tracks are provided within the confines of said border line of said article surface to be traced successively, and said selected pixels are arranged along said search track and symmetrically on the opposite sides of said flag point to define an extended mask including more than one symmetrical pair of said pixels; and wherein said analyzing step comprises sub-steps of:

determining, in accordance with the corresponding pixels in said original grey value image, an individual difference between the grey values of said pixels in said each symmetrical pair;

summing said individual grey value differences determined for all of said symmetrical pairs to obtain a sum grey value difference;

comparing said sum grey value difference with a predetermined reference value to designate said flag point as a defect indicative point when said sum grey value difference is above said reference value;

comparing the number of said defect indicative points determined on said one search track with a predetermined reference number to designate said one search track as a defect indicative track when the number of said defect indicative points exceeds said reference number;

successively tracing another one of said search track to determine whether said another search track is designated as said defect indicative track;

judging that the presence of a defect when the said defect indicative tracks are designated successively for the adjacent ones of said search tracks and the number of said defect indicative tracks exceeds a predetermined number.

6. An optical surface inspection method for inspecting a surface defect such as a crack, stain, and irregularity of an article, said method comprising the steps of:

illuminating said article surface;

acquiring an original grey value image of an illuminated region including said article surface, said original grey value image comprising a number of pixels having individual grey values;

processing said original grey value image to acquire an edge image which comprises a number of corresponding pixels having binary values representing a border line of said article surface and an edge indicative of a possible defect within said border line;

providing, in said edge image, at least one inspection zone within the confines of said border line of said article surface;

scanning said inspection zone to define an initial flag point at the pixel which is firstly detected to represent said edge;

tracing along said edge from said initial flag point to designate a series of the flag points of the pixels arranged in the direction of said edge;

selecting, in the vicinity of each of said flag points, a plurality of the pixels arranged in a direction crossing said edge direction;

analyzing, in accordance with the corresponding pixels in said original grey value image, the grey values of said selected pixels as to whether there is a critical change in the grey values between said selected pixels for evaluation of the presence of the defect.

7. A method as set forth in claim 6, wherein said selected pixels are arranged symmetrically on the respective sides of said flag point so as to define an extended mask of said selected pixels for said each flag point; and said method further including a step of:

providing, within the confines of said border line of the article surface, a reference zone in order to determine a reference grey value which is an average of the grey values of the corresponding pixels in said original grey value image to those within said reference zone; and wherein said analyzing method further comprising sub-steps of:

comparing the gray value of each selected pixels in said each extended mask with said reference grey value;

determining, in accordance with the corresponding pixels in said original grey value image, a grey value difference between the selected pixels in symmetrical pair within said each mask;

comparing said grey value difference for said each mask with a predetermined white threshold;

comparing said grey value difference for said each mask with a predetermined black threshold;

designating, for each mask, said grey value difference as a white index when all of said selected pixels in said mask have the grey values above said reference grey value and said grey value difference is above said white threshold;

designating, for each mask, said grey value difference as a black index when any one of said selected pixels in said mask has the grey value below said reference grey value and said grey value difference is below said black threshold;

summing said white or black indexes obtained for the individual masks to provide a white or black sum;

comparing said white or black sum with a predetermined white or black reference for evaluation of the presence of a light or dark defect within said inspection zone.

8. A method as set forth in claim 6, wherein said selected pixels are arranged symmetrically on the respective sides of said flag point so as to define an extended mask of said selected pixels for said each flag point; and wherein said analyzing method further comprising sub-steps of: determining, in accordance with the corresponding pixels in said original grey value image, a grey value difference between the selected pixels in symmetrical pair within said each mask;

comparing said grey value difference for each mask with a predetermined threshold to designate said flag point as a defect indicative point when said grey value difference is above said threshold;

summing said defect indicating points obtained for the individual masks defined with regard to the series of said flag points;

obtaining, in accordance with the corresponding pixels in said original grey value image, for each of said pixels defining said flag points, a maximum absolute gradient of the grey level determined relative to the neighboring pixels;

summing said maximum absolute gradient obtained for all the flag points; and judging the presence of defect within said inspection zone when the total number of said defect indicating points exceeds a predetermined threshold number or when the sum of said absolute maximum values exceeds a predetermined threshold value.

9. A method as set forth in claim 6, wherein said selected pixels comprise a pair of the pixels arranged symmetrically on the respective sides of each one of said flag points; and wherein said method further including a step of:

provizing, within the confines of said border line of the article surface, a reference zone in order to determine a reference grey value which is an average of the grey values of the corresponding pixels in said original grey value image to those within said reference zone; and wherein defining a white level reference which is greater than said reference grey value;

defining a black level reference which is less than said reference grey value;

obtaining, in accordance with the corresponding pixels in said original grey value image, the greater grey value and the smaller grey value of the two pixels in said one symmetrical pair defined for each of said flag points;

comparing, for said each one symmetrical pair of the pixels, said greater grey value with said white level reference and designating the corresponding flag point as a white defect indicative point when said greater grey value exceeds said white level reference;

comparing, for said each one symmetrical pair of the pixels, said smaller grey value with said black level reference and designating the corresponding flag point as a black defect indicative point when said smaller grey value is below said black level reference;

counting the number of said white defect indicating points as well as the number of the black defect indicating points designated for said flag points;

judging the presence of the defect within said inspection zone either when the total number of said white defect indicating points exceeds a predetermined number or when the total number of said black defect indicating points exceeds a predetermined number.

10. A method as set forth in claim 6, wherein said article surface is illuminated from a direction inclined with respect thereto such that said edge may represent poor contrast around a surface defect such as a minute projection and depression appearing on or in the article surface; and wherein said analyzing step further comprises sub-steps of:

determining a center point on which the series of said flag points are substantially centered;

providing, in accordance with the corresponding pixels in said original grey value image, a grey value distribution along an inspection line passing through said center point along said illuminating direction to said article surface;

extracting, from said grey value distribution, a maximum grey value from a continuous set of grey values exceeding above a predetermined white level reference and a minimum grey value from a continuous set of grey values which fall below a predetermined black level reference and which appear within a predetermined distance from said maximum grey value along said inspection line;

obtaining a difference between said maximum and minimum grey values so as to compare the resulting difference with a predetermined value and judge the presence of the surface irregularity when said difference exceeds said predetermined value.

11. A method as set forth in claim 10, wherein said white level reference is defined to be greater by a suitable extent than an average grey value determined for a reference zone selected within said original grey value image in correspondence to a defect-free zone of said article surface, and said black level reference is smaller than by a suitable extent than said average grey value.

* * * * *